US00PP09894P

United States Patent [19]

Vanderlaan

[11] Patent Number: Plant 9,894

[45] Date of Patent: May 13, 1997

[54] SYNGONIUM PLANT NAMED 'BOB WHITE'

[75] Inventor: Dan H. Vanderlaan, Lake Worth, Fla.

[73] Assignee: Vanderlaan Brothers, Lake Worth, Fla.

[21] Appl. No.: 581,484

[22] Filed: Dec. 29, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,663 10/1996 Klinger ..... Plt./88.1

*Primary Examiner*—James R. Feyrer

*Attorney, Agent, or Firm*—Foley & Lardner

[57] ABSTRACT

A new and distinct cultivar of *Syngonium podophyllum* named 'Bob White', particularly characterized by its striking greenish white foliage, compact branched growth habit, and absence of vining growth.

2 Drawing Sheets

The present invention comprises a new and distinct cultivar of *Syngonium podophyllum* known by the cultivar name 'Bob White'. The new cultivar is an unusual mutation discovered among a tissue culture-derived group of plants of Syngonium 'Lemon Lime'.

The new cultivar 'Bob White' was discovered by inventor Dan H. Vanderlaan, Lake Worth, Fla., in February 1993. The new cultivar was recognized for its unusual leaf color and its compact, branched habit when compared to the cultivar 'White Butterfly' and the parent cultivar 'Lemon Lime', both unpatented. Syngonium 'White Butterfly' is well known in the horticultural trade for its white and green marked foliage, and attractive vining habit. Syngonium 'Lemon Lime', also very well known in the horticultural trade, is distinguished by its green foliage with white markings, and its short highly branched compact growth habit.

Horticultural evaluation by the inventor of subsequent generations of propagation by tissue culture carried out under the direction of the inventor at Lake Placid, Fla. beginning in March 1994, has clearly demonstrated that the combination of characteristics as herein disclosed for 'Bob White' are firmly fixed and are retained through successive generations of asexual reproduction.

Syngonium 'Bob White' has not been observed under all possible environmental conditions. The phenotype may vary significantly with variations in environment such as temperature, light intensity and day length without, however, any variation in genotype. The following observations, measurements and comparisons describe plants grown by the inventor in Lake Worth, Fla. under greenhouse conditions which approximate those commonly used in commercial practice.

The following traits have been repeatedly observed and are determined to be basic characteristics of 'Bob White' which, in combination, distinguish it from the commercial cultivars 'White Butterfly' and 'Lemon Lime':

1. The leaves of 'Bob White' are almost entirely greenish white. By comparison, both 'White Butterfly' and 'Lemon Lime' have considerably more green markings and fewer white markings than 'Bob White'.

2. Plants of 'Bob White' have similar horticultural traits as 'Lemon Lime'. However, 'Bob White' requires approximately 5% more time to reach salable size.

3. Unlike 'White Butterfly', which has relatively few axillary branches and a vining growth habit, 'Bob White' has more axillary branches and a compact growth habit, similar to the parent cultivar 'Lemon Lime'. Plants of 'Bob White' maintain their unique leaf coloration with age. By comparison, older, larger plants of both 'Lemon Lime' and 'White Butterfly' produce leaves with increasing amounts of green and fewer white markings.

In the accompanying color photographic drawing, the color photograph on sheet 1 illustrates a plant of 'Bob White' approximately 6 months in age growing in a 15.2 cm pot.

The color photograph on sheet 2 comprises a top perspective view of plants of 'Bob White', 'White Butterfly', and 'Lemon Lime', all of which are approximately 6 months in age and growing in 15.2 cm pots. The new cultivar 'Bob White' is on the lower right, 'White Butterfly' at the top, and 'Lemon Lime' at the lower left. The differences noted above will be readily apparent from the comparison photograph.

Attached hereto is Table I, which compares 'Bob White', 'Lemon Lime', and 'White Butterfly' with respect to the characteristics listed.

The following description is based on observations and measurements of 'Bob White' grown in greenhouses in Lake Worth, Fla. Color references are made to The Royal Horticultural Society Colour Chart.

DESCRIPTION OF THE PLANT

Botanical: *Syngonium podophyllum* c.v. 'Bob White'.

Origin: Spontaneous mutation, discovered among tissue culture-derived plants of 'Lemon Lime'.

Form/shape: Compact, branched habit, particularly suitable for 10 cm–15 cm pots and baskets.

Growth: Vigorous growth; however, 5% slower to attain marketable size than comparable plants of 'Lemon Lime'.

Stem: Diameter 0.8 cm–1.1 cm, oval in cross-section.

Roots: Green to brown thick fleshy roots 1.2 mm–2.0 mm thick.

Foliage:

*Quantity*.—Abundant.

*Shape*.—The leaf is ovate in shape with an acuminate tip and a sagittate to hasate base. The leaf margin is wavy.

*Size*.—Mature lead blades are approximately 17.5 cm to 20 cm long from leaf tip to tip of lobes, approximately 7.2 cm to 8.5 cm wide at the juncture of the petiole, and approximately 11.1 cm to 13.0 cm long from the apex to the junction of the petiole. The leaf has two long pointed lobes which extend past the junction of the leaf and petiole. The distance from the leaf/petiole junction to the highest point on the lobes is approximately 5.6 cm to 7.1 cm. Length/width ratio is approximately 2.4. Thickness is approximately 0.2 mm at the thinnest part between the major veins.

*Gloss.*—Matte.

*Color.*—Mature leaves Upper surface — Whiter than, but closest to 194C, with occasional flecks of 146A, margin 137A. When juvenile, the leaves have considerably more green (137A) markings, particularly along the leaf margin. Lower surface — 146C-D. Newly unfurled leaves Upper surface — 145C-D, with flecks of 144A. Lower surface — 145B C.

*Petioles.*—4 mm in diameter at the apex of the sheath.

*Veins.*—The veins are recessed, and the leaf blade is convex between the veins on the upper surface. The veins protrude from the underside of the leaf.

Disease resistance: Similar to that of parent cultivar 'Lemon Lime'.

TABLE 1

| PARAMETER | BOB WHITE | LEMON LIME | WHITE BUTTERFLY |
|---|---|---|---|
| Adventitious Roots diameter | 0.5 mm–1.0 mm | 0.8 mm–1.1 mm | 0.8 mm–1.0 mm |
| Stem Diameter | 0.8 cm–1.1 cm | 0.6 cm–0.9 cm | 0.7 cm–0.9 cm |
| Leaf Length - leaf apex to longest lobe | 17.5 cm–20 cm | 14.0 cm–15.3 cm | 14.2 cm–16.4 cm |
| Leaf Width - at junction of petiole | 7.2 cm–8.5 cm | 7.0 cm–8.5 cm | 7.6 cm–8.6 cm |
| Length/Width Ratio | 2.4 | 1.9 | 1.8 |
| Leaf Thickness - between veins | 0.2 mm | 0.1 mm | 0.1 mm |
| Number of branches with at least one leaf. | 8 | 10 | 5 |
| Petiole Diameter - at junction of sheath | 3.6 mm–4.0 mm | 3.5 mm–3.9 mm | 3.0 mm–4.0 mm |

I claim:

1. A new and distinct variety of *Syngonium podophyllum* named 'Bob White', as illustrated and described.

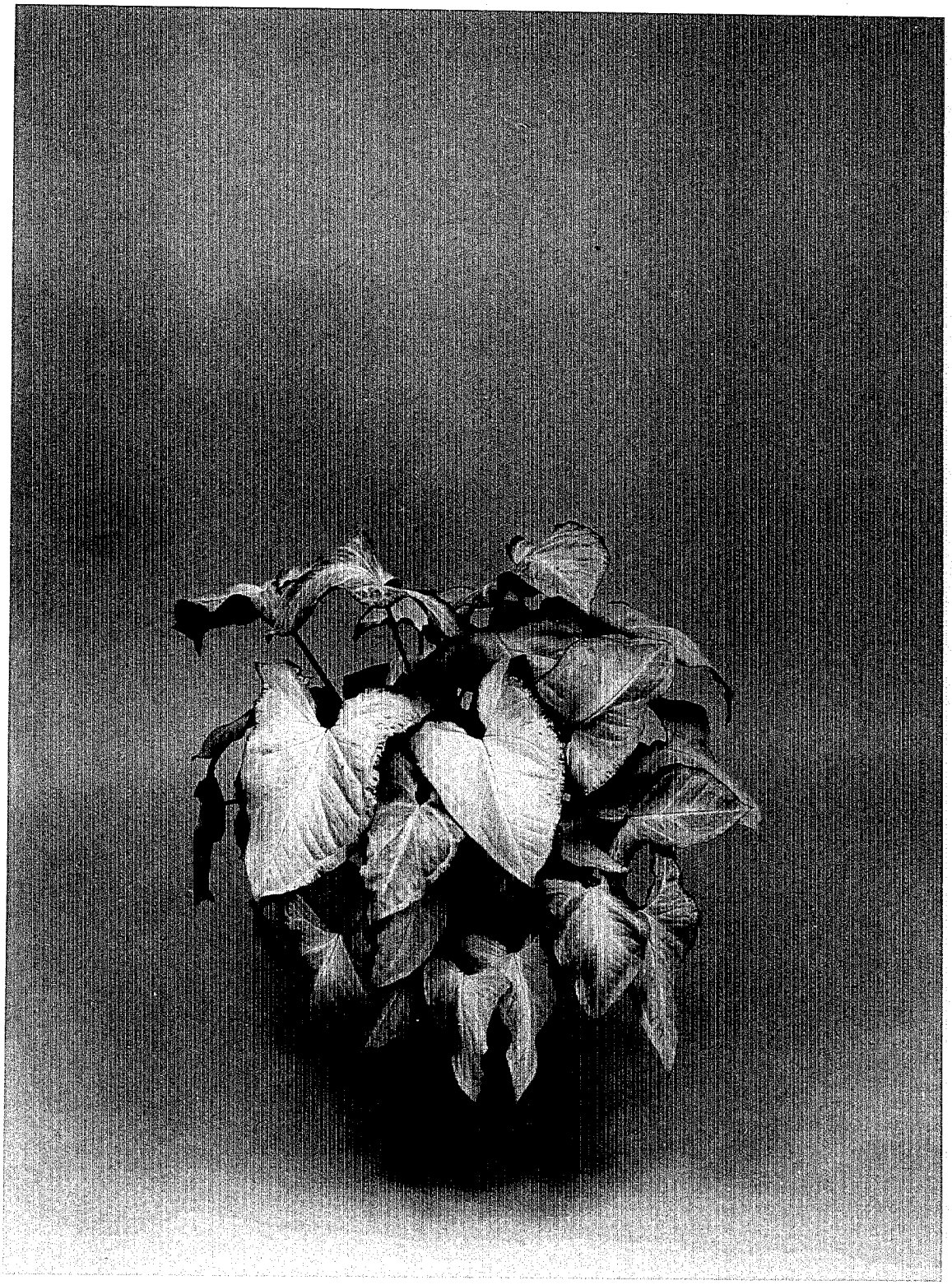

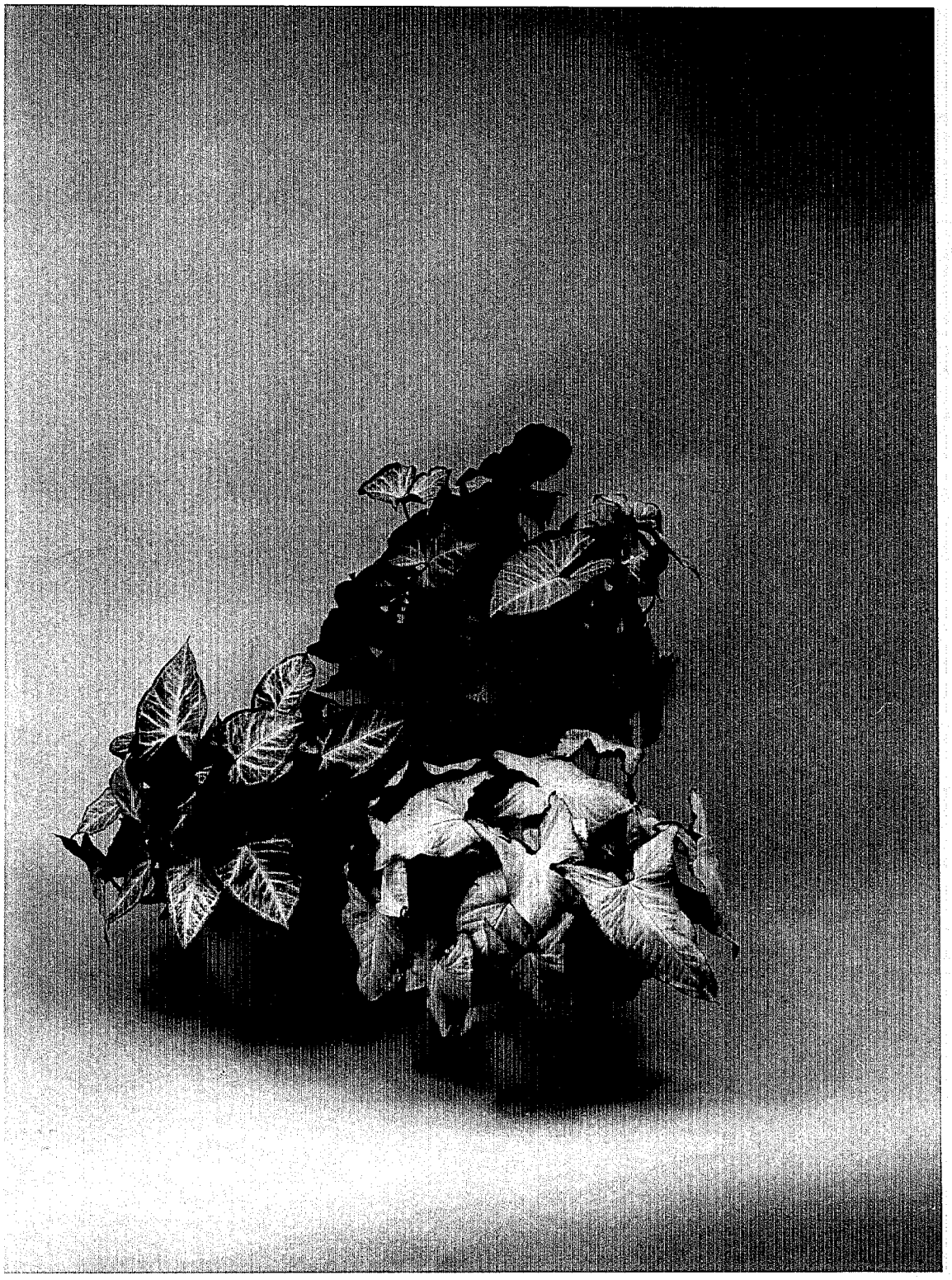

* * * * *